United States Patent [19]

Wiita et al.

[11] 4,351,342

[45] Sep. 28, 1982

[54] BALLOON CATHETER

[76] Inventors: Bruce E. Wiita, Box 3669, Jupiter, Fla. 33458; J. Michael Teets, 12104 Gardenway G-7, Palm Beach Gardens, Fla. 33410

[21] Appl. No.: 272,127

[22] Filed: Jun. 10, 1981

[51] Int. Cl.³ .......................................... A61M 25/00
[52] U.S. Cl. .................................. 128/349 B; 128/344
[58] Field of Search ............. 128/349, 349 B, 349 BU, 128/344, 246, 325

[56] References Cited

U.S. PATENT DOCUMENTS

| | | | |
|---|---|---|---|
| 2,649,092 | 8/1953 | Wallace | 128/349 |
| 2,919,697 | 1/1960 | Kim | 128/349 |
| 3,045,677 | 7/1962 | Wallace | 128/349 |
| 3,190,291 | 6/1965 | Foley | 128/349 |
| 3,344,791 | 10/1967 | Foderick | 128/349 |
| 3,438,375 | 4/1969 | Ericson | 128/349 |
| 3,811,448 | 5/1974 | Morton | 128/349 B |
| 3,954,110 | 5/1976 | Hutchison | 128/349 B |
| 3,982,544 | 9/1976 | Dyck | 128/349 R |
| 4,022,216 | 5/1977 | Stevens | 128/349 B |
| 4,157,094 | 6/1979 | Patel | 128/349 B |
| 4,211,233 | 7/1980 | Lin | 128/349 B |
| 4,219,026 | 8/1980 | Layton | 128/349 B X |
| 4,233,983 | 11/1980 | Rocco | 128/349 |

Primary Examiner—Stephen C. Pellegrino
Attorney, Agent, or Firm—Roylance, Abrams, Berdo & Farley

[57] ABSTRACT

A catheter comprising an elongated tube and an inflatable balloon. The elongated tube has a wall defining a main lumen in its interior. The distal end of the tube is insertable within a body while its proximal end remains exteriorally of the body. A port extends through the tube wall to provide fluid communication between the main lumen and the exterior of the tube at the distal end of the tube. The inflatable balloon has an opening extending through its side, which opening is aligned with the port in the tube. The peripheries of the opening in the balloon and of the port in the tube are completely adhered. An inflation lumen is also provided in the tube which conducts fluid pressure to and from the interior of the balloon to inflate and deflate the balloon. This arrangement enables the inflated balloon to cushion fully the distal end of the catheter and provide a tapered lead in to the port to enhance drainage.

20 Claims, 27 Drawing Figures

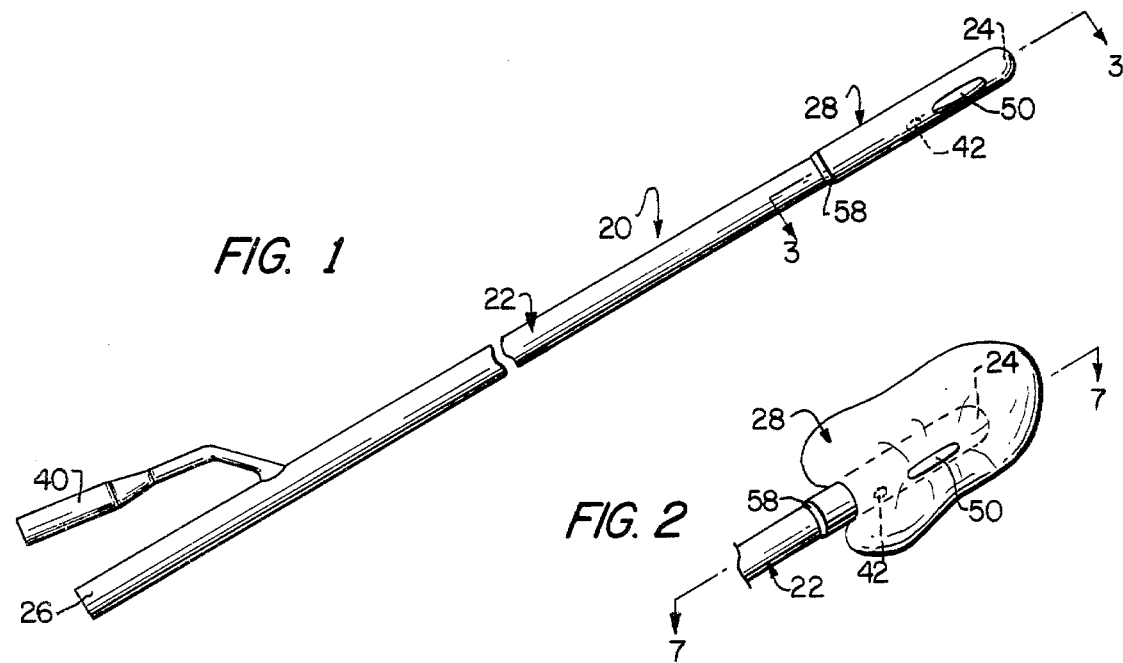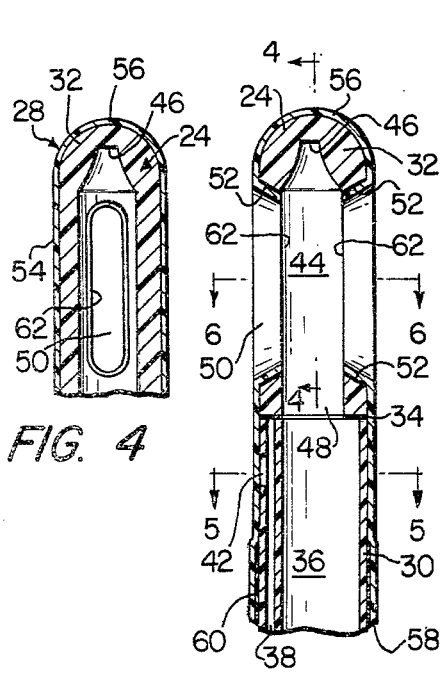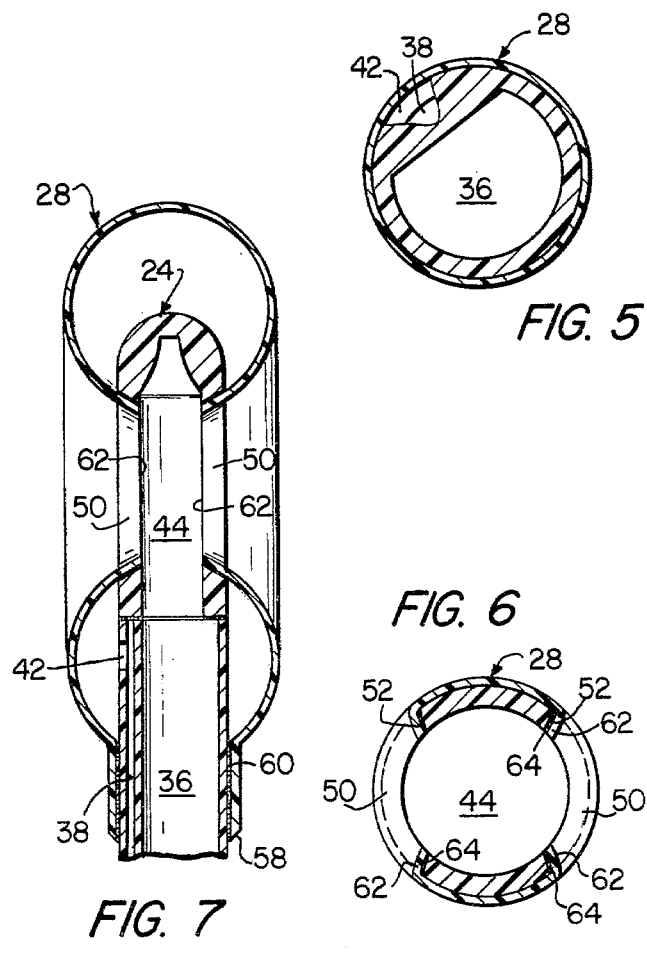

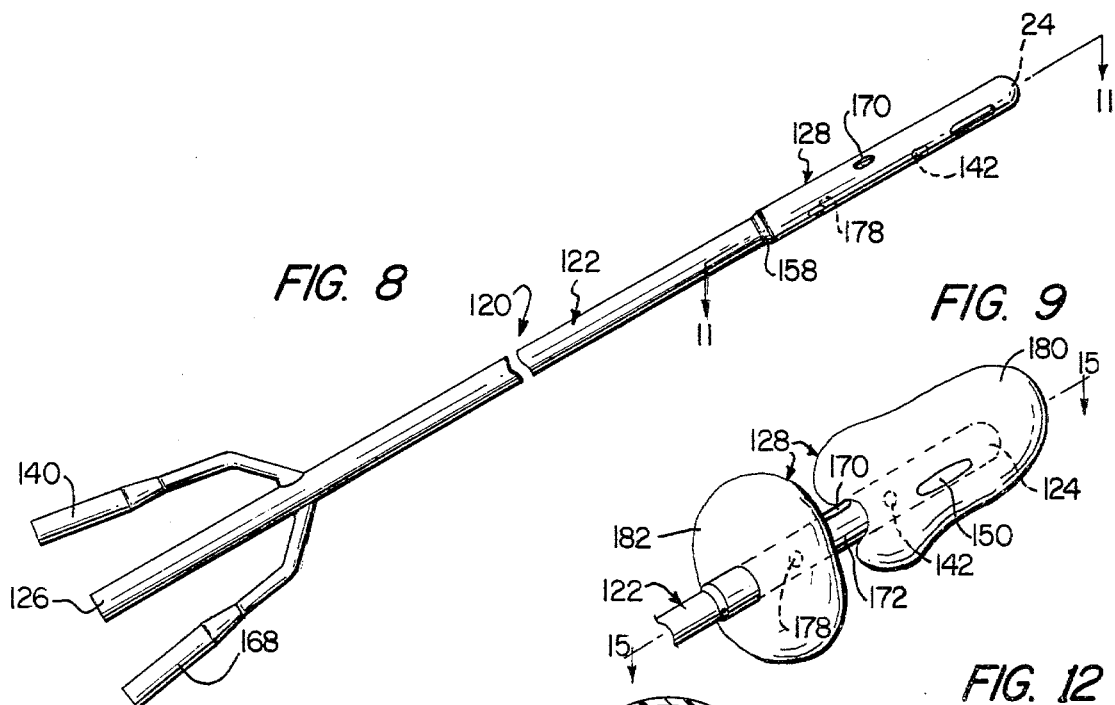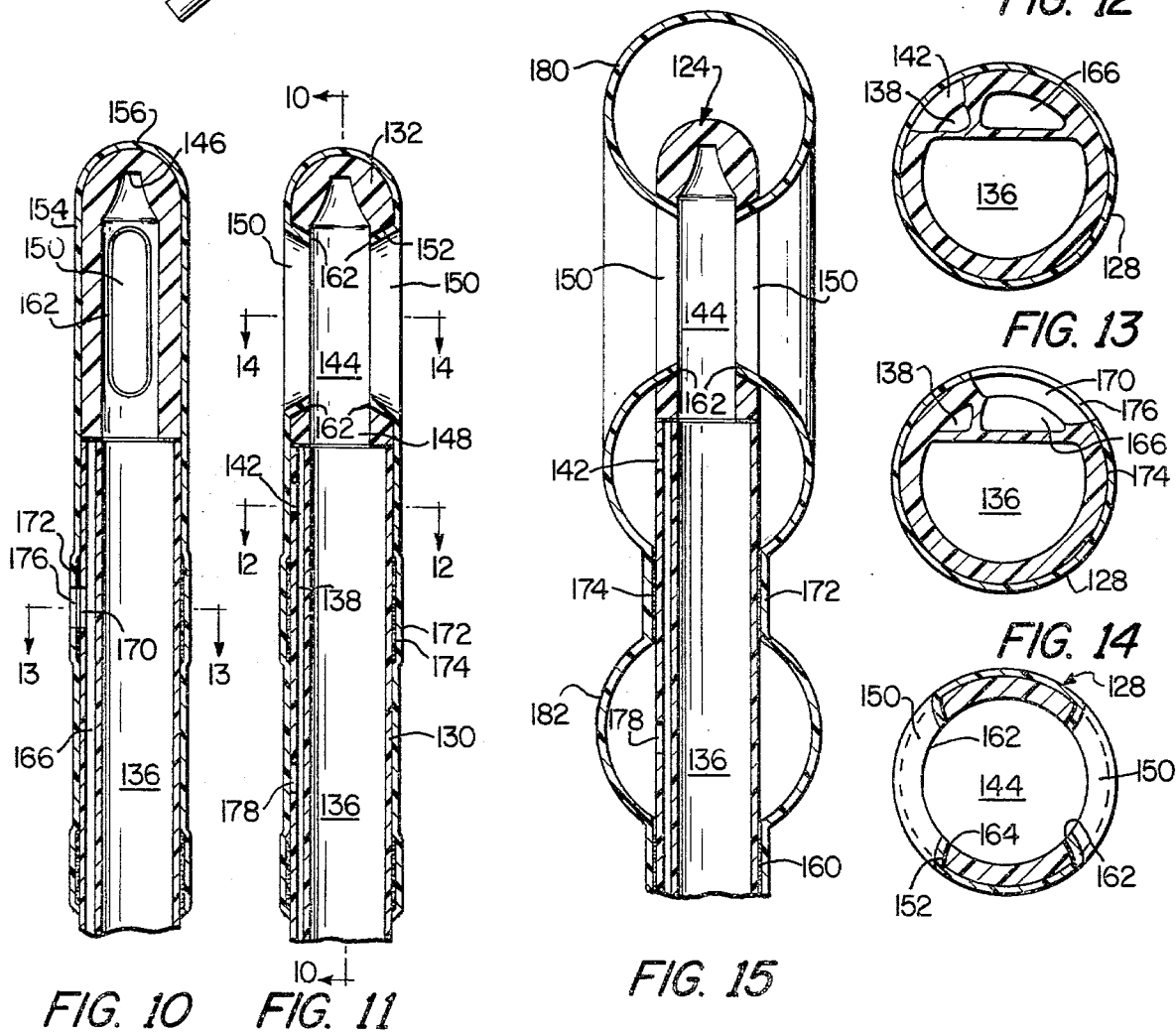

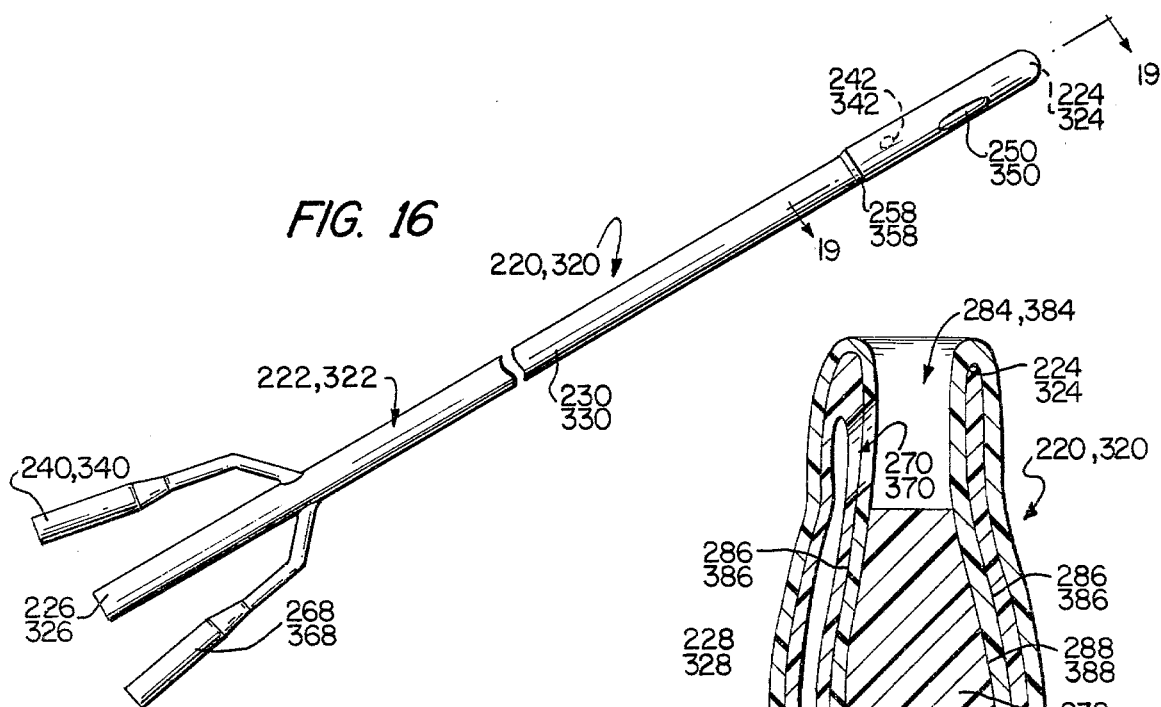
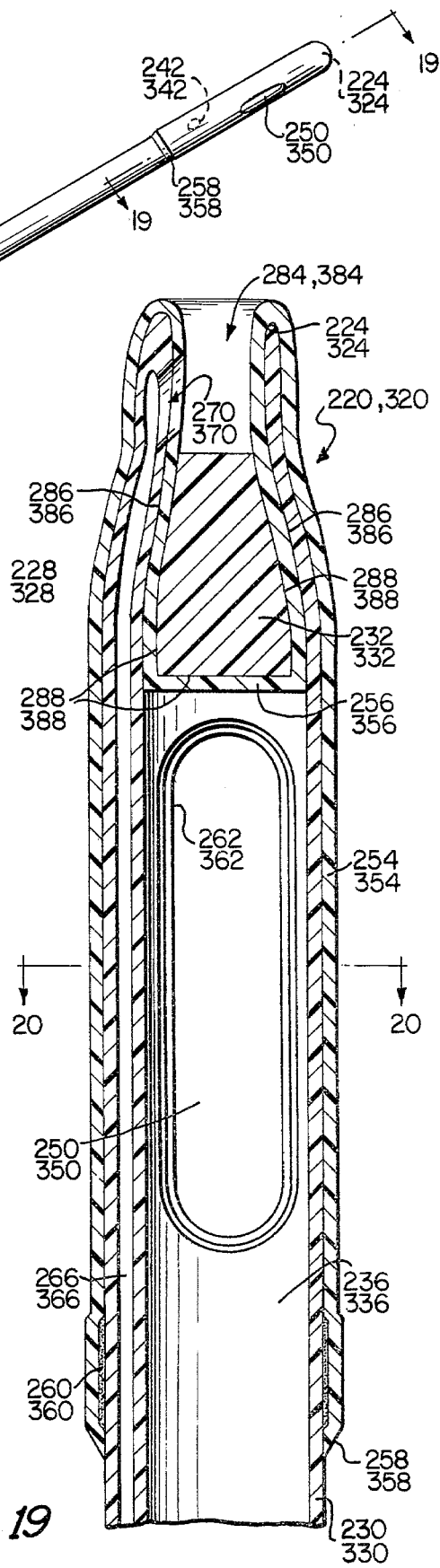
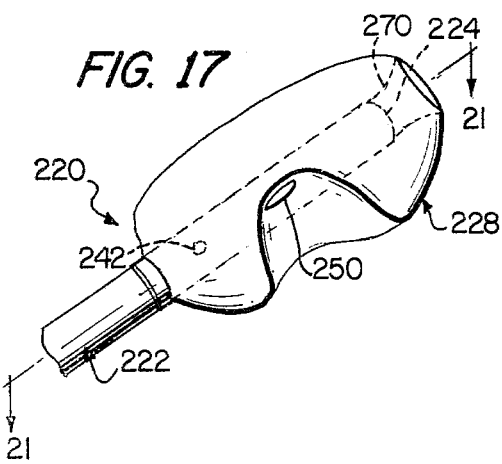
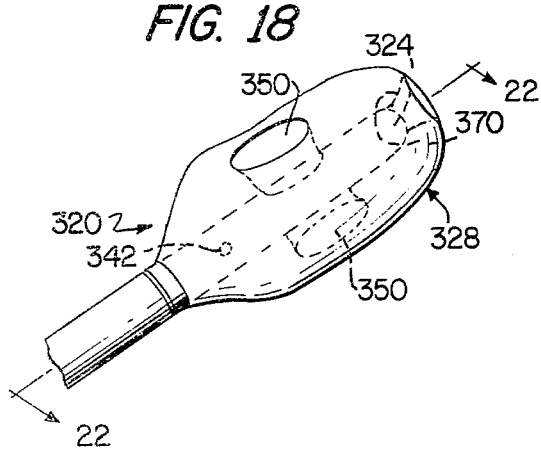

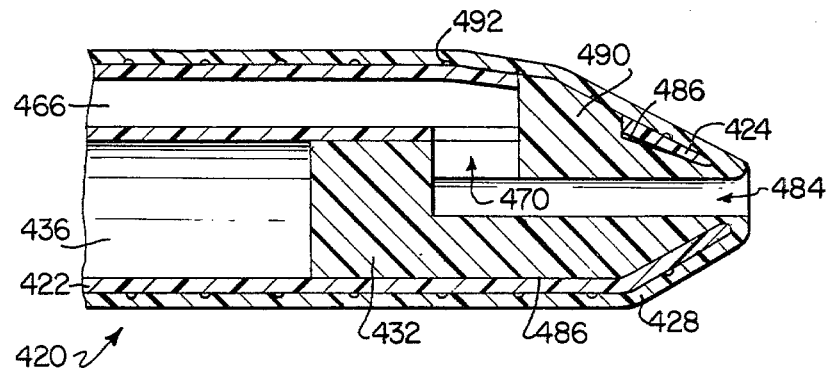
FIG. 23
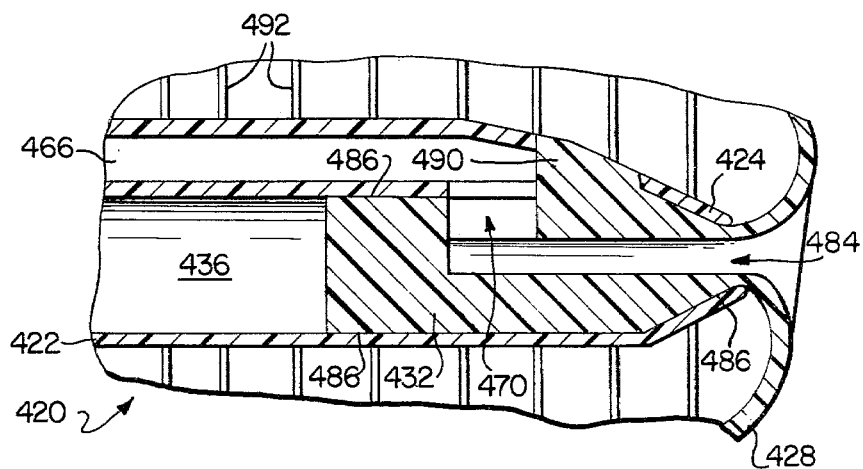
FIG. 24
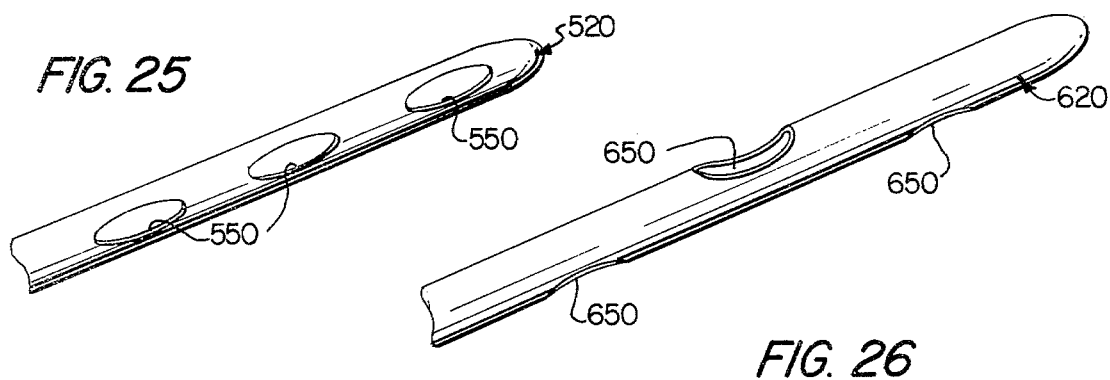
FIG. 25
FIG. 26

BALLOON CATHETER

BACKGROUND OF THE INVENTION

1. Field of the Invention

The present invention relates to a catheter having an inflatable balloon at one of its ends for retaining the catheter within a patient's body. More particularly, the present invention relates to a balloon catheter wherein the catheter tube has a port adjacent its distal end, and the inflatable balloon has an opening aligned with the port and is secured to the tube such that the adjacent peripheries of the port and opening are adhered together to provide an inflated cushion completely about the port and the tube distal end and a tapered lead in for the port.

2. Description of the Prior Art

Catheters comprising an elongated flexible tube with an inflatable balloon attached to the tube at its distal end are often used to drain urine from a patient's bladder. The distal end of the catheter is inserted through the urethra and positioned such that the drainage ports and the inflatable balloon are inside the bladder and its proximal end is outside the patient's body. The balloon is then inflated to secure the catheter distal end in the bladder. The drainage ports are in fluid communication with a drainage lumen extending in the tube to permit urine to drain from the bladder and into a container coupled to the catheter proximal end.

A variety of balloon arrangements have been employed in conventional catheters. Typical examples are disclosed in U.S. Pat. Nos. 4,022,216, Stevens; 3,438,375, Ericson; 3,954,110, Hutchison; and 4,157,094, Patel.

The Stevens patent discloses a catheter having two inflatable balloons located on opposite sides of oblong inlet openings in the catheter tube. Each balloon is supplied with an inflating fluid through separate passageways. The balloons are secured to the catheter tube at locations spaced from the edges of the inlet openings in the tube.

The Ericson patent discloses a variety of balloon catheter configurations. In FIGS. 1-17, a single balloon is located within the tube inlet opening located on the side or open upper end of the catheter tube such that upon inflation, the tube extends around only a portion of the tube inlet opening. In FIGS. 18 and 19, the balloon is attached to the catheter tube at locations adjacent to, but spaced from, a single catheter tube inlet opening. In FIGS. 20–21, the balloon is spiral in shape and covers inlet openings in the catheter tube.

The Hutchison patent discloses a catheter with a balloon which is attached to the end of a catheter tube, but which only surrounds the upper and lateral edges of the inlet openings in the catheter tube. The extreme distal ends of the balloon and tube are cemented together so that the tip is not cushioned upon inflation of the balloon.

The Patel patent discloses another conventional balloon shape which is located only below the inlet opening in the tube. In this catheter, the tip is formed from a separate member from the tube and is secured thereto by means of an adhesive.

These devices suffer from numerous disadvantages. For example, the two balloons of the Stevens patent which are spaced from the ports in the tube do not cushion the tube, provide a tapered inlet, prevent organ tissue from being suctioned into the tube and drain the organ adequately. In a similar manner, the Ericson, Hutchison and Patel patents do not provide sufficient protection from the reinforced tip of the tube and/or do not have balloons which completely surround the tube inlet opening to protect the tissue adjacent to the opening and to facilitate drainage.

Furthermore, these conventional catheters are relatively complex in arrangement and are difficult and expensive to manufacture.

SUMMARY OF THE INVENTION

Accordingly, it is an object of the present invention to provide a catheter having a tube and an inflatable balloon mounted at the tube distal end, and with a port in the tube and an aligned opening in the balloon secured together at their peripheries such that upon inflation of the balloon, the inflated balloon completely surrounds the tube port and envelopes the distal end of the tube.

Another object of the present invention is to provide a balloon catheter which is completely cushioned around the peripheries of the inlet openings to dampen contact between the organ and the catheter, to provide a tapered lead in to the ports to facilitate drainage and to prevent drawing of the body tissue into the catheter tube.

A further object of the present invention is to provide a balloon catheter of rugged construction which is inexpensive and simple to manufacture.

The foregoing objects are obtained by providing a catheter comprising an elongated tube and an inflatable balloon. The elongated tube has a wall which defines a main lumen therein, a distal end insertable into a body and a proximal end located outside of the body. A port extends through the tube wall providing fluid communication between the main lumen and the exterior of the tube. The port is located adjacent the distal end of the tube and is defined by edges. The balloon has a tubular portion, one closed end and one opened end. The distal end of the tube is enveloped by the balloon with the open end of the balloon adhered about the tube on the side of the port remote from the tube distal end. An opening extends through the tubular portion of the balloon and is aligned with the port with its periphery completely adhered to the side edges of the port. An inflation lumen conducts inflating fluid pressure to and from the balloon to control inflation.

By attaching the balloon to the catheter tube in this manner, the catheter distal end, which is placed within the body organ, is completely cushioned at its end and sides, and particularly about the inlet port. This cushioning prevents trauma and inflamation of the body organ by the tip and prevents disruptions of suture lines following surgery. Moreover, attaching the periphery of the balloon opening to the edges of the tube port forms a tapered lead in for the port upon balloon inflation, which enhances drainage. Still further, the cushioning spaces the inlet port from the body organ tissue preventing such tissue from being suctioned into the catheter tube.

Additionally, this manner of securing the balloon to the tube facilitates manufacture of the catheter.

Other objects, advantages and salient features of the present invention will become apparent from the following detailed description which, taken in conjunction with the annexed drawings, discloses preferred embodiments of the present invention.

BRIEF DESCRIPTION OF THE DRAWINGS

Referring to the drawings which form a part of this original disclosure:

FIG. 1 is a perspective view illustrating a catheter in accordance with the first embodiment of the present invention, prior to inflation of the balloon;

FIG. 2 is a fragmentary, perspective view of the catheter of FIG. 1 after inflation of the balloon;

FIG. 3 is a fragmentary, side elevational view of the catheter of FIG. 1 in cross-section taken along lines 3—3 in FIG. 1;

FIG. 4 is a fragmentary, side elevational view of the catheter of FIG. 1 in cross-section taken along lines 4—4 in FIG. 3;

FIG. 5 is a cross-sectional view of the catheter of FIG. 1 taken along lines 5—5 in FIG. 3;

FIG. 6 is a cross-sectional view of the catheter of FIG. 1 taken along lines 6—6 in FIG. 3;

FIG. 7 is a cross-sectional view of the catheter of FIG. 1 taken along lines 7—7 in FIG. 2;

FIG. 8 is a perspective view illustrating a catheter in accordance with a second embodiment of the present invention, prior to inflation of the balloon;

FIG. 9 is a fragmentary, perspective view of the catheter of FIG. 8 after inflation of the balloon;

FIG. 10 is a fragmentary, side elevational view of the catheter of FIG. 8 in cross-section taken along lines 10—10 in FIG. 11;

FIG. 11 is a fragmentary, side elevational view of the catheter of FIG. 8 in cross-section taken along lines 11—11 in FIG. 8;

FIG. 12 is a cross-sectional view of the catheter of FIG. 8 taken along lines 12—12 in FIG. 11;

FIG. 13 is a cross-sectional view of the catheter of FIG. 8 taken along lines 13—13 in FIG. 10;

FIG. 14 is a cross-sectional view of the catheter of FIG. 8 taken along lines 14—14 in FIG. 11;

FIG. 15 is a partial, side elevational view of the catheter of FIG. 8 in cross-section taken along lines 15—15 in FIG. 9;

FIG. 16 is a perspective view illustrating a catheter in accordance with the third and fourth embodiments of the present invention, prior to inflation of the balloon;

FIG. 17 is a fragmentary, perspective view of the catheter in accordance with the third embodiment of the present invention after inflation of the balloon;

FIG. 18 is fragmentary, perspective view of the catheter in accordance with the fourth embodiment of the present invention after inflation of the balloon;

FIG. 19 is a fragmentary, side elevational view of the catheter in accordance with the third and fourth embodiments of the present invention in cross-section taken along lines 19—19 of FIG. 16;

FIG. 23 is a fragmentary, side elevational view in cross section illustrating a catheter in accordance with a fifth embodiment of the present invention prior to inflation of the balloon;

FIG. 24 is a fragmentary, side elevational view in cross section of the catheter of FIG. 23 after inflation of the balloon; and FIGS. 25 and 26 are fragmentary, perspective views of catheters in accordance with further embodiments of the present invention, prior to inflation of the balloons.

DETAILED DESCRIPTION OF THE PREFERRED EMBODIMENTS OF THE INVENTION

Figure 20A:
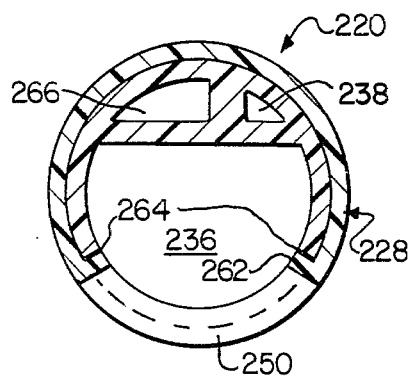
FIGS. 20A and 20B are cross-sectional views of the catheter in accordance with the third and fourth embodiments of the present invention taken along lines 20—20 of FIG. 19.
Figure 20B:
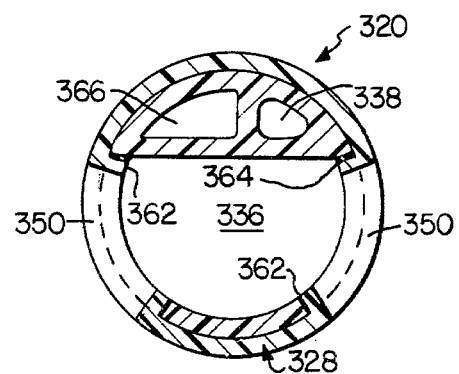

Referring initially to the first embodiment of the present invention illustrated in FIGS. 1-6, and referring particularly to FIGS. 1 and 2, the catheter 20 of the present invention is primarily intended for use as a urinary catheter for draining the bladder of a patient. Basically, catheter 20 comprises an elongated tube 22 having an upper, distal end 24 and a lower, proximal end 26. Distal end 24 is adapted to be placed within a patient's organ (e.g., a bladder) while proximal end 26 remains outside the body to receive the fluids drained from the body or to deliver the fluids injected in the body.

Distal end 24 of tube 22 is enveloped by a balloon 28. Balloon 28 is secured to tube distal end 24 and is inflatable to the configuration illustrated in FIG. 2.

Tube 22 comprises a flexible, relatively long hose 30 and a tip member 32 which are fixedly joined end to end by a suitable adhesive, annular strip 34 as seen in FIG. 3. The interior of hose 30 is divided into two passageways, a main lumen 36 and an inflation lumen 38, as illustrated in FIG. 5. Each lumen extends for the entire length of the hose. A suitable coupling can be mounted in proximal end 26 for coupling main lumen 36 in fluid communication with apparatus such as a container to store fluids drained from the body cavity or a pump to inject fluids into the body. In a suitable, conventional manner, a coupling 40 is mounted in the lower end of inflation lumen 38 for connecting inflation lumen 38 to a fluid pressure source to supply fluid pressure to and release fluid pressure from lumen 38. Adjacent the upper end of inflation lumen 38, an inflation aperture 42 extends through the outer wall of inflation lumen 38 to provide fluid communication between inflation lumen 38 and the exterior of hose 30.

Tip member 32 has thicker walls than those of hose 30 making it more rigid to facilitate insertion of the catheter through a urethra and to prevent collapse during operation. The interior of tip member 30 is hollow to define an internal cavity 44 with a closed upper end 46 and an open lower end 48. Cavity 44 and open end 48 are aligned with main lumen 36 and are in fluid communication therewith. Closed upper end 46 provides an abutment against which a metal rod can be positioned for pushing the catheter through the patient's urethra and into the bladder.

Two oblong or elongated ports 50 are formed in the sides of tip member 32 to provide fluid communication between internal cavity 44 and the exterior of the catheter. Ports 50 are elongated in the axial direction of tip member 32 and are defined by peripheral edges 52 which taper inwardly.

A single, unitary, inflatable balloon 28 is mounted on and envelopes distal end 24 of tube 22. Balloon 28 comprises a tubular portion 54, an upper closed end 56 and an open lower end 58. The portion of balloon 28 adjacent open end 58 is adhered to the exterior surface of tube 22 below ports 50 (i.e., on the side of ports 50 remote from distal end 24) by an adhesive area 60.

Inlet openings 62 are formed in tubular portion 54 of balloon 28. These openings are oriented and shaped to align and mate with ports 50 in tip member 32. The entire periphery of each balloon inlet opening 62 is adhered to one of the peripheral edges 52 of tube ports 50 by adhesive 64 to seal completely the interior of balloon 28 from cavity 44 and main lumen 36. In this manner, balloon 28 is adhered to tube 22 solely between the peripheries of balloon openings 62 and tube port edges 52 and between balloon open end 58 and the adjacent portion of tube 22. The remaining portions of balloon 28 are free to move and expand relative to tube 22 upon inflation thereof.

In operation, the catheter 20 is inserted within a patient's bladder in the collapsed condition illustrated in FIG. 1 with distal end 24 located within the bladder and proximal end 26 located outside of the body. Coupling 40 is then coupled to a conventional fluid pressure source to supply fluid pressure into inflation lumen 38. The fluid pressure passes through inflation lumen 38 and inflation aperture 42 and into the interior of balloon 28 causing balloon 28 to inflate to the configuration illustrated in FIGS. 2 and 7.

In the inflated condition of balloon 28, balloon 28 fully protects the patient from the trauma and inflamation normally caused by distal end 24 of catheter 20 and enhances the operation thereof. The top of tip member 32 is fully cushioned by the upper portion of balloon 28. Since the peripheries of inlet openings 62 are completely adhered to edges 52 of ports 50, cushioning is provided completely around ports 50 to prevent the patient's organ tissue from being suctioned into the catheter to avoid damage to such tissue. Moreover, such cushioning of ports 50 provides a tapered lead in to the ports to convey fluid into the catheter, thereby enhancing drainage of the organ. The lowermost portion of the inflated balloon (i.e., that portion located between the lowermost portion of ports 50 and adhesive area 60) can be employed to seal the bladder from the prostate region enhancing use of this catheter during post prostate operation recovery.

When catheter 20 is to be removed from the patient, the fluid pressure within inflation lumen 38 is relieved through coupling 40. The relief of the fluid pressure permits balloon 28 to contract to the FIG. 1 configuration. After deflation of balloon 28, catheter 20 may be easily removed from the patient.

FIGS. 8-14 illustrate a second embodiment of the present invention. The portions of the second embodiment which are similar to those of the first embodiment are denoted with a like reference numeral preceded with the number 1.

Catheter 120 is different from catheter 20 in that catheter 120 has been modified to supply fluid to the bladder while simultaneously draining the bladder in order to flush the bladder. This additional function is provided in catheter 120 by modifying hose 130 and balloon 128.

In catheter 120, a supply lumen 166 is formed within the interior of hose 130 in addition to main lumen 136 and inflation lumen 138. The lower end of supply lumen 166 is coupled to and is in fluid communication with a coupling 168 for attaching it to a suitable mechanism capable of forcing fluid into and through supply lumen 166. A supply aperture 170 is formed in an outer wall of hose 130 providing fluid communication between the interior of supply lumen 166 and the exterior of hose 130.

The single, unitary balloon 128 is somewhat longer than balloon 28 and extends for a further distance along the length of tube 122. An intermediate, cylindrical portion 172 of balloon 128 is adhered to an adjacent cylindrical portion of the exterior of hose 130 by a suitable adhesive area 174. Supply aperture 170 extends through this adjacent cylindrical portion of tube 130. Cylindrical portion 172 has an opening 176 which is aligned with and of the same shape as aperture 170 forming a continuation thereof. Aperture 170 and opening 176 permit fluid passing through supply lumen 166 to exit from hose 130 and into the patient.

An additional inflation aperture 178 is formed in hose 130 below cylindrical portion 172. This inflation aperture is similar to inflation aperture 142, and to aperture 42 in catheter 20. Inflation aperture 178 provides fluid communication between inflation lumen 138 and the interior of balloon 128 between cylindrical portion 172 and area 160.

Catheter 120 operates similar to catheter 20. The fluid pressure passing through inflation lumen 138 and inflation apertures 142 and 178 causes balloon 128 to inflate to the configuration illustrated in FIGS. 9 and 15. Intermediate cylindrical portion 172 divides the inflated balloon into an upper section 180 and a lower section 182. Upper section 180 is similar to the inflated balloon configuration of catheter 20. The adhesion of cylindrical portion 172 by adhesive 174 to hose 130 provides a constricted section of the inflated balloon where supply aperture 170 is located. Lower section 182 is located below this constricted section and above lower open end 158, and functions to seal off the prostate area from the bladder and to space supply aperture 170 up into the bladder to facilitate the supplying of fluid into the bladder, for example, to wash blood and clots out of the bladder to prevent clogging of the catheter with the clots.

Once balloon 128 is fully inflated, fluid (e.g., water) may be pumped through supply lumen 166 and aperture 170 and opening 176 and into the patient's bladder. The water and urine then drain into ports 150, through cavity 144 and main lumen 136 and out of the patient to flush the bladder. Catheter 120 may be removed from the patient after relieving fluid pressure through coupling 140. This will permit balloon 128 to deflate and resume the configuration of FIG. 8.

FIGS. 16-22 illustrate third and fourth embodiments of the present invention. The portions of the third and fourth embodiments which are similar to those of the first embodiment are denoted with a like reference numeral preceded with the numbers 2 and 3, respectively. The portions of the third and fourth embodiments which are similar to those of the second embodiment are denoted with a similar reference numeral in which the first digit 1 is replaced with a 2 or 3, respectively.

Catheters 220, 320 are similar to catheter 120 in that catheters 220, 320 are adapted to supply fluid to the bladder while simultaneously draining the bladder in order to flush the bladder. However, the arrangements at the distal ends of hoses 230, 330 and balloons 228, 328 have been modified.

In catheters 220, 320, hoses 230, 330 have the same cross sectional configuration as hose 130 of catheter 120 in that they include main lumens 236, 336, inflation lumens 238, 338 and supply lumens 266, 366. The lower ends of supply lumens 266, 366 are coupled to and in fluid communication with couplings 268, 368 for attaching them to a suitable mechanism capable of forcing fluid into and through supply lumens 266, 366. The supply apertures 270, 370 are formed adjacent distal ends 224, 324 of tubes 222, 322 in the tube walls and the balloons to provide fluid communication between the exterior of the tubes and balloons. The main difference between catheter 220 and catheter 320 is that catheter 220 has a single port, while catheter 320 has two ports.

Figure 21:
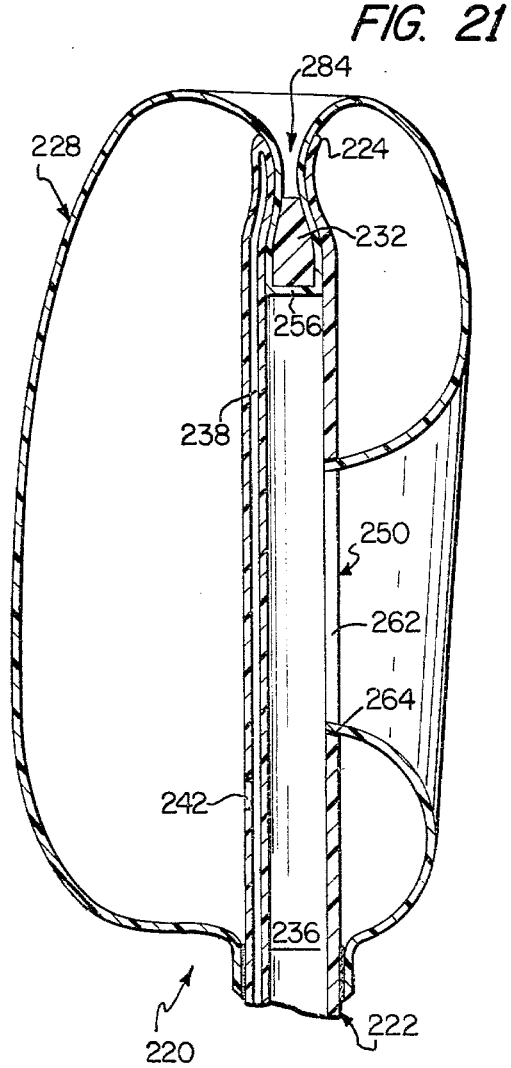
FIG. 21 is a partial, side elevational view of the catheter of FIG. 17 in cross-section taken along lines 21—21 thereof.
Figure 22:
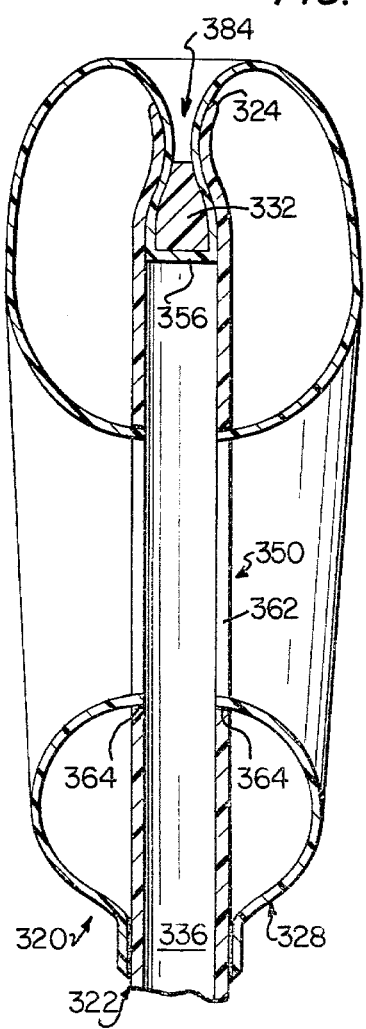
FIG. 22 is a partial, side elevational view of the catheter of FIG. 18 in cross-section taken along lines 22—22 thereof.

Catheters 220, 320 do not include the tip members 32, 132 of the catheters of the first and second embodiments. Instead, distal ends 224, 324 of hoses 230, 330 are suitably treated to close inflation lumens 238, 338 and supply lumens 266, 366 at the distal ends thereof, as illustrated in FIGS. 19, 21 and 22.

The single, unitary balloons 228, 328 on these catheters are attached at their open ends 258, 358 by adhesive areas 260, 360 and at balloon openings 262, 362 and ports 250, 350 by adhesive 264, 364, as in the first embodiment. The ends of the balloons remote from open ends 258, 358 extend over distal ends 224, 324 of tubes 222, 322 and into main lumens 236, 336 such that closed ends 256, 356 of the balloons are spaced from the distal ends of the tubes. In this manner, closed ends 256, 356 extend into the upper portions of main lumens 236, 336 to define cavities 284, 384 at the distal ends of the catheters which cavities are isolated from main lumens 236, 336. Closed ends 256, 356 are spaced between the catheter distal ends and ports to avoid interference with drainage through the ports and main lumens, while closing the distal ends of the main lumens. The adjacent surfaces of the balloon closed ends and of the internal surfaces of the tubes defining the upper portions of the main lumens are bonded by suitable adhesive 286, 386.

Reinforcing plugs 232, 236 are fixed within the lower portions of the sections of the balloons which extend within the catheter tubes and are fixed thereto by adhesive 288, 388 placed between their contacting surfaces. The reinforcing plugs are made of relatively rigid plastic material and are generally frustroconical in shape tapering towards the distal ends of the catheters.

In making the catheters, the distal end areas of tubes 222, 322 are trimmed to a taper by means of a tapering tool contracting the balloons and tubes about the plugs until the adhesive therebetween is cured. Once that adhesive has cured, supply aperture 270 can be formed within balloons 228, 328 and tubes 222, 322 to provide fluid communication between supply lumens 266, 366 and cavities 284, 384. The distal ends of the inflation and supply lumens can then be suitably plugged, e.g., by adhesive. The balloons are positioned over the tubes and are secured by adhesive about ports 250, 350 and at open ends 258, 358.

Catheters 220, 320 operate similarly to catheter 120. Fluid pressure passing through the inflation lumens and the inflation apertures cause the balloons to inflate. The inflation of catheter 220 is illustrated in FIGS. 17 and 21, while the inflation of catheter 320 is illustrated in FIGS. 18 and 22. By providing the supply apertures 270, 370 in the distal ends of the catheters, such that the irrigation fluid passes out the distal ends of the catheters, the drainage ports 250, 350 can be located closer to the bottom of the bladder, thereby enhancing its drainage. Since the balloons line and are adhered to cavities 284, 384, the balloons upon inflation form tapered exit areas and provide cushioning about the catheter distal ends. The lowermost portions of the inflated balloons can function to seal off the prostate area from the bladder.

Once balloons 228, 328 are fully inflated, fluid (e.g., water) may be pumped through supply lumens 266, 366 and apertures 270, 370 and into the patient's bladder. The water and urine are then drained into ports 250, 350 and main lumens 236, 336 and out of the patient to flush the bladder. Catheters 220, 320 can be removed from the patient after relieving fluid pressure through couplings 240, 340. This will permit balloons 228, 328 to deflate and resume the configuration illustrated in FIG. 16.

FIGS. 23 and 24 illustrate a fifth embodiment of the present invention. The portions of the fifth embodiment which are similar to those of the first embodiment are denoted with a like reference numeral preceded with the number 4. Those portions of the fifth embodiment which are similar to those of the second, third and fourth embodiments are denoted with a similar reference numeral in which the first digit 1, 2 or 3, respectively, is replaced with a 4.

Catheter 420 is similar to catheters 220, 320 since it supplies fluid to the bladder while simultaneously draining the bladder to flush the bladder and since its supply aperture 470 is located adjacent distal end 424 of tube 422. However, the connection of balloon 428 and plug 432 and the form of supply aperture 470 and plug 432 have been modified.

In catheter 420, tube 422 has the same cross sectional configuration as tubes 222, 322 of catheters 220, 320. The lower end of supply lumen 466 is coupled to and in fluid communication with a suitable mechanism for forcing fluid into and through supply lumen 466. The single unitary balloon 428 is attached at its open end and at the port or ports as in the first, third or fourth embodiments.

Balloon 422 and plug 432 are unitarily formed as a single member with the balloon extending from the distal end of the plug and over distal end 424 and the exterior of tube 422. The adjacent areas of balloon 428 and plug 432 and of the internal surfaces of tube 422 defining the upper portion of main lumen 436 are bonded by a suitable adhesive 486. Supply aperture 470 extends radially through a central portion of plug 432 to provide fluid communication between cavity 484 in the plug and supply lumen 466. A radially extending projection 490 is located above supply aperture 470 and is mounted in an opening in tube 422 such that it extends over supply lumen 466.

The internal surface of balloon 428 has a plurality of circumferential recesses 492 which enhance uniform expansion of the balloon. These recesses may be formed in the balloons of the other embodiments.

Since the operation of catheter 420 is identical to that of catheters 220, 320, it will not be described in detail.

FIGS. 25 and 26 illustrate catheters 520, 620, respectively, having more than two ports. In catheter 520, ports 550 are aligned. In catheter 620, ports 650 are staggered.

By forming the catheters of the present invention in this manner, the internal organ of the patient is fully protected from trauma and inflamation which can be caused by direct contact with the tip member. This cushioning permits the tip to be relatively stiff to facilitate insertion of the catheter and to prevent collapse of the catheter during operation. Moreover, this cushioning is so arranged to enhance drainage of the bladder by enhancing the flow of fluid into the drainage ports.

Additionally, the construction of the catheters of the present invention facilitate their manufacture. Since the inflation lumen and the supply lumen of each catheter extends the entire length of each hose, the hoses can be manufactured simply and inexpensively by extrusion as currently done. The distal ends of the hoses can be closed by the separate tip members and by the adhesive used to secure the tip members to the hoses. The single, unitary balloon further enhances and facilitates the attachment of the tip member and the hose, as well as simplifying the attachment of the balloon to the tube.

While particular embodiments have been chosen to illustrate the invention, it will be understood by those skilled in this art that various changes and modifications can be made therein without departing from the scope of the invention as defined in the appended claims.

What is claimed is:

1. A catheter, comprising:
    an elongated tube having a wall defining a main lumen therein, a distal end insertable into a body and a proximal end;
    at least one port extending through said wall providing fluid communication between said main lumen and the exterior of said tube, said port being defined by edges and being located adjacent said distal end;
    an inflatable balloon having a tubular portion, one closed end and one open end, said balloon being mounted on and enveloping said tube distal end, and being adhered to said tube on the side of said port remote from said distal end about said open end;
    at least one opening extending through said tubular portion of said balloon and aligned with said port and being defined by a periphery, said periphery of said opening being completely adhered to said edges of said port; and
    an inflation lumen in said tube for conducting fluid pressure to and from said balloon.

2. A catheter according to claim 1, wherein only a single balloon is provided.

3. A catheter according to claim 1, wherein said balloon is unitary.

4. A catheter according to claim 1, wherein a lower portion of said balloon above said open end adhered to said tube provides means for sealing off a patient's prostate area upon inflation of said balloon.

5. A catheter according to claim 1, wherein said edges of said port tapers inwardly.

6. A catheter according to claim 1, and further comprising
    a supply lumen in said tube for conveying fluid into the body; and
    a supply aperture in said tube wall providing fluid communication between said supply lumen and the exterior of said tube.

7. A catheter according to claim 6, wherein said balloon has a cylindrical portion spaced from said ends thereof which is adhered to said tube, and said supply aperture extends through said cylindrical portion and said tube wall adjacent thereto.

8. A catheter according to claim 7, wherein said balloon has upper and lower inflatable sections separated by said cylindrical portion, and said inflation lumen is in fluid communication with each said section through separate inflation apertures formed in said tube wall.

9. A catheter according to claim 7, wherein two ports defined by edges extend through said wall adjacent said distal end and two openings defined by peripheries extend through said tubular portion of said balloon in alignment with said ports; and wherein said balloon is adhered to said tube only between said balloon opening peripheries and said tube port edges, between said balloon cylindrical portion and an adjacent portion of said tube, and between said balloon open end and an adjacent portion of said tube.

10. A catheter according to claim 1, wherein two ports defined by edges extend through said wall adjacent said distal end and two openings defined by peripheries extend through said tubular portion of said balloon in alignment with said ports; and wherein said balloon is adhered to said tube only between said balloon opening peripheries and said tube port edges and between said balloon open end and an adjacent portion of said tube.

11. A catheter according to claim 1, wherein said tube comprises a tip member and a flexible hose coupled thereto, and said balloon extends over the juncture therebetween.

12. A catheter according to claim 1, wherein two ports defined by edges extend through said wall adjacent said distal end and two openings defined by peripheries extend through said tubular portion of said balloon in alignment with said ports.

13. A catheter according to claim 1, and further comprising:
    a supply lumen in said tube for conveying fluid into the body; and
    a supply aperture in said tube wall and said balloon providing fluid communication between said supply lumen and the exterior of said tube and said balloon.

14. A catheter according to claim 13, wherein said supply aperture is located between said distal end of said tube and said port.

15. A catheter according to claim 13, wherein a plug is fixed in said main lumen between said distal end and said port to close said main lumen thereat, and said supply aperture is located between said plug and said distal end.

16. A catheter according to claim 15, wherein said plug is spaced within said main lumen to define a cavity thereabove opening on said distal end.

17. A catheter according to claim 16, wherein said closed end of said balloon extends into said cavity, and lines and is adhered to said tube in said cavity.

18. A catheter according to claim 17, wherein said supply aperture opens into said cavity.

19. A catheter according to claim 15, wherein said plug is formed of relatively rigid material.

20. A catheter according to claim 1, further comprising
    a supply lumen in said tube for conveying fluid into the body;
    a plug attached to said balloon and fixed in said main lumen adjacent said distal end to close said main lumen thereat; and
    a supply aperture in said tube wall and said plug providing fluid communication between said supply lumen and the exterior of said tube and said balloon.

* * * * *